United States Patent [19]

Nickerson

[11] Patent Number: 5,827,944
[45] Date of Patent: Oct. 27, 1998

[54] SAMPLE SCREENING AND PREPARATION WITHIN A COLLECTION VESSEL

[75] Inventor: Mark A. Nickerson, Landenberg, Pa.

[73] Assignee: Hewlett-Packard Company, Palo Alto, Calif.

[21] Appl. No.: 602,673

[22] Filed: Feb. 16, 1996

[51] Int. Cl.[6] .................................................. C12Q 1/68
[52] U.S. Cl. .............................................. 73/23.41; 435/6
[58] Field of Search ........................... 73/23.41, 23.36, 73/23.37, 23.38, 23.39, 23.4, 23.42; 435/6

[56] References Cited

U.S. PATENT DOCUMENTS

| | | | |
|---|---|---|---|
| 3,966,410 | 6/1976 | Jahnsen | 23/230 |
| 4,017,597 | 4/1977 | Reynolds | 424/1.5 |
| 4,944,781 | 7/1990 | Ruggirello et al. | 55/386 |
| 5,363,707 | 11/1994 | Augenblick et al. | 73/864.84 |
| 5,453,380 | 9/1995 | Poole et al. | 436/174 |

FOREIGN PATENT DOCUMENTS

WO91/15745  10/1991  WIPO.

OTHER PUBLICATIONS

Zhouyao Zhang and Janusz Pawliszyn, University of Waterloo, Waterloo Ontario, Canada "Headspace Solid–Phase Microextraction" Copyright 1993 American Chemical Society.

Primary Examiner—Scott W. Houtteman
Attorney, Agent, or Firm—Richard Schuette

[57] ABSTRACT

A method and apparatus for sample screening and sample preparation within a vessel sealed with a cap, the vessel having at least a portion of the inside surface coated with a stationary phase having an affinity for analytes of interest. A sample possibly containing such analytes is introduced into the vessel whereby the analytes of interest migrate out of the sample and into the stationary phase for detection by a screening device and for desorption.

19 Claims, 4 Drawing Sheets

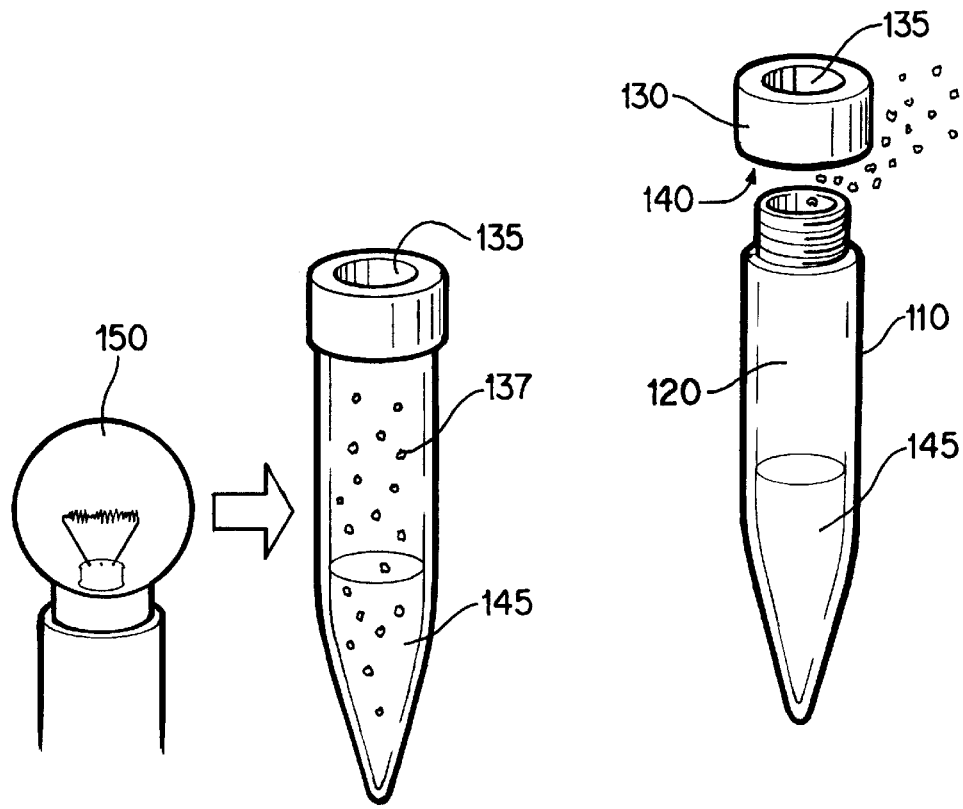
FIG. 1a
FIG. 1b
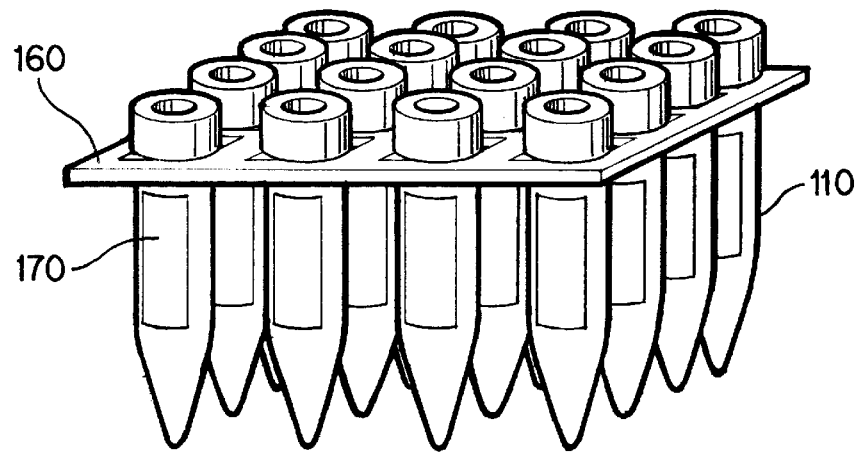
FIG. 1c

SAMPLE SCREENING AND PREPARATION WITHIN A COLLECTION VESSEL

FIELD OF THE INVENTION

The present invention relates to methods and apparatus for screening and preparation of an organic sample for introduction into an analytical instrument and, more particularly, to screening and preparation of a sample within the vessel in which the sample was initially collected.

BACKGROUND OF THE INVENTION

Chromatography is a preferred method for the analysis of impurities and contaminates ("analytes of interest") found in a sample. In particular, gas chromatography is particularly good for separation and analysis of environmental samples having analytes of interest that are typically not complex molecules. Prior to the introduction of a sample into a chromatographic instrument, the sample must be prepared such that analytes of interest can be extracted from the sample.

Extraction is defined as a chemical or physical process for drawing the analytes of interest out from a sample. Traditional means of extraction involve mixing an immiscible extraction solvent with the sample such that analytes of interest are thermodynamically driven to dissolve into the solvent to achieve equilibrium based on the relative solubility of the sample and the solvent. At equilibrium, molecules of each analyte of interest cross the interface between the sample and extracting solvent at the same rate in both directions. This is termed "dynamic equilibrium". The extracting fluid may also be a gas wherein solubility of the analytes refers to their respective vapor pressures. The solvent, containing dissolved components can then be aspirated or otherwise removed for detection by a spectrographic device or injection into a chromatographic device.

Solid phase extraction (SPE) is a technique which utilizes a flow-through chamber that contains a large number of small inert silica particles each coated with a stationary phase material. The liquid sample is flushed through the cartridge and the analytes of interest diffuse into the stationary phase coating. A solvent having a high solubility factor for the analytes of interest is then flushed through the cartridge, thereby dissolving and carrying away the analytes of interest for analysis. The Hewlett-Packard 7686 PrepStation System is an example of a system that provides for fully automated SPE.

A technique for carrying out Solid Phase Micro extraction (SPME) without the use of liquid or gaseous solvent is disclosed in International Application Number PCT/CA91/00108 entitled "Method and Device for Solid Phase Micro extraction and Desorption" by Janusz B. Pawliszyn. A solid or hollow fused silica fiber coated with a stationary phase is attached to the plunger mechanism of a standard syringe such that the fiber can be extended from inside the hollow syringe needle. The needle is inserted through a septum and into a vial. The plunger is depressed so that the fiber will extend into the sample such that the analytes of interest diffuse into the stationary phase coating until equilibrium is reached, whereupon, the fiber is withdrawn into the needle and the needle is withdrawn from the sample vial. The needle is then inserted through a septum and into the injection port of a gas chromatograph for thermal desorption and cryofocusing the analytes of interest onto the column.

The quantity of analytes of interest that are absorbed into the stationary phase is directly related to the surface area and thickness of the stationary phase. Increasing film thickness to increase capacity has the detrimental effect of slowing the rate of equilibration within the stationary phase. Another problem occurs during the transport of the fiber from the sample to the trap as volatiles may be lost and contaminants from the lab may be gained.

U.S. Pat. No. 5,453,380 entitled "Thin Film Sample Preparation" discloses a method and apparatus for enhancing the speed and precision of extracting analytes of interest from a solid, liquid or a suspension/emulsion sample matrix. The sample matrix is formed into a thin, uniform film so as to maximize the surface area for a given sample volume. Maximizing the surface area in contact with the solvent increases the rate at which the analytes of interest come into equilibrium between the sample matrix and the solvent. Thin film sample preparation may also include the step of forming, on the inside surface of a sample vessel, a thin film of a compound having an affinity for analytes of interest or an affinity for contaminants in the sample matrix. After contact with the sample, one or more solvents can then be used to wash and/or extract analytes of interest from the sample matrix.

U.S. Pat. No. 5,363,707 entitled "Headspace Sampling System" describes a number of techniques for collecting gases from the sample headspace of a sealed sample container. The sample matrix is heated in the presence of a gaseous extracting solvent such that analytes of interest are allowed to come into equilibrium in the gas phase. Inserting a dispense needle into the headspace of the sample vial provides for aspiration of a portion of the gaseous extracting solvent containing components of interest.

There exists a need for a method and apparatus for field screening through which large number of samples can be collected outside of the laboratory and effectively screened such that only those samples having analytes of interest are brought back into the laboratory for analysis.

There also exists a need for a sample preparation method and apparatus that provides for both sample collection and sample preparation in the same vessel, thereby eliminating the need to transfer the sample and to reduce the loss of volatiles.

There exists a need for a sample preparation method that does not require the use of solvents, that is environmentally cleaner and lower in cost than traditional solvent based sample preparation methods.

A need also exists for reducing sources of contamination from laboratory air, glassware, collection vessels and solvents.

It would be desirable and of considerable advantage to provide a method for sample preparation that reduces extraction and desorption times and increases the robustness of chromatographic analysis. Further, such a sample preparation method could be advantageous when implemented by use of a single vessel for both collection and sample preparation, especially if the new sample preparation method provided an improvement in any of the following areas: elimination of the loss of volatiles, reduction in the contamination from laboratory air, glassware, vessels and solvents, reduction in the plugging and/or corruption of results with samples having high solid contents.

It will be apparent from the foregoing that there is still a need for a solventless method for sample screening and sample preparation in one vessel that is not susceptible to contamination.

SUMMARY OF THE INVENTION

The invention provides a method and apparatus for screening and preparation of a sample matrix within a sealed vessel. At least a portion of the inside surface of the vessel is coated with a stationary phase having an affinity for analytes of interest. A sample is introduced into the vessel such that analytes within the sample have the opportunity to migrate into the stationary phase. A screening device that illuminates the analytes in the stationary phase may be employed for ascertaining whether analytes of interest have been adsorbed.

The analytes of interest are desorbed from the stationary phase for introduction into an analytical instrument for quantification. Desorption may be effected by orienting the vessel such that an airspace forms above the sample and in contact with the stationary phase. Highly volatile analytes of interest desorb directly into the air space and an equilibrium is established within the vessel. The vessel may be heated to speed up the rate of desorption of the less volatile analytes from the stationary phase. The vessel is sealed with a cap having a septum such that a sampling needle may be employed for aspirating the headspace for introduction into a gas chromatograph. The invention advantageously provides for the preparation of the sample within a closed vessel such that there is no loss of volatile analytes of interest and/or contamination.

Accordingly, the invention advantageously provides for screening and preparation of a sample within a collection vessel to minimize the possibility of contamination and loss of volatiles. Other aspects and advantages of the present invention will be come apparent from the following detailed description, taken in conjunction with the accompanying drawings, illustrated by way of example the principles of the invention.

BRIEF DESCRIPTION OF THE DRAWINGS

FIG. 1a is a simplified schematic representation of a vessel having a stationary phase coating on the inside surface of the cap.

FIG. 1b is a simplified schematic representation of the vessel in FIG. 1a being screened for components of interest.

FIG. 1c is a simplified schematic representation of a plurality of screened vessels as illustrated in FIG. 1b ready for transport.

FIG. 4a depicts an alternative embodiment in which microwave energy is employed for heating a sample in a vessel as depicted in FIG. 1a.

DETAILED DESCRIPTION OF THE PREFERRED EMBODIMENTS

Figure 2A:
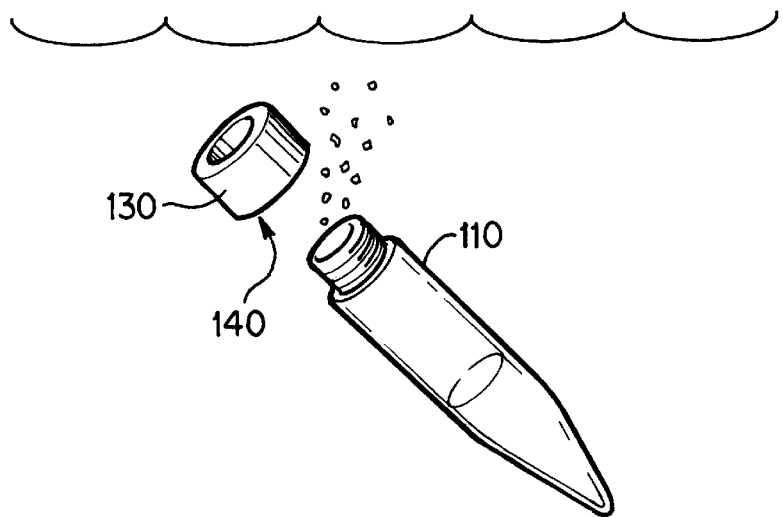
FIG. 2a depicts the vessel of FIG. 1a being filled with a liquid sample.

The invention provides a method and apparatus for solventless screening and preparation of a sample within a vessel coated on an inner surface with a stationary phase having an affinity for analytes of interest. The invention minimizes or eliminates many problems associated with prior art sample preparation techniques including contamination, loss of volatile analytes and dependence on the use of solvents.

In the preferred embodiment, the invention provides a method and apparatus for preparation of a sample in a sealed vessel having a stationary phase coating that adsorbs analytes of interest. The vessel is sealed with a cap having a septum for providing access to the vessel. After adsorption, the vessel is oriented such that analytes of interest may be desorbed from the stationary phase coating into the headspace for aspiration by a sampling needle and for injection into the gas chromatograph.

With reference now to the drawings wherein like reference numerals designate corresponding parts throughout the several views, FIG. 1a illustrates a vessel 110 being employed for ground water analysis. The vessel 110 is filled with a ground water sample 120 by immersion in a supply of ground water. A thermally conductive cap 130 is applied to the vessel and ensures that the sample and any volatiles analytes of interest do not escape from the vessel. A septum 135 is employed for accessing the head space 137 formed between the inside of the cap and the top of the sample 120. Cap 130 may include a stationary phase coating 140 having an affinity for volatile and semi-volatile analytes of interest. Alternatively, a stationary phase coating 145 may be employed on the bottom portion of the vessel. Polydimethylsiloxane is an example of a stationary phase having an affinity for those analytes of interest typically found in ground water. International Application Number PCT/CA91/00108 entitled "Method and Device for Solid Phase Microextraction and Desorption" hereby incorporated by reference, discloses alternative stationary phase coatings having known affinities for different analytes of interest and methods for attaching them to a fused silica fibre. These alternative stationary phase coatings may be employed in the present invention and attached to the vessel in the same manner in which they are attached to a fibre. The thickness of the stationary phase coating and the amount of surface covered may vary with the desired application.

Most samples are ionic solutions, having a neutral or somewhat basic PH level providing an environment likely to degrade analytes of interest. Liberation of these analytes chemically bonded to the sample and adsorption of them into the stationary phase is enhanced by adjusting the pH (eg. by adding NaOH, HCL or NaCl) which makes the analytes less soluble in the sample matrix as the analytes seek a more favorable environment away from an ionic solution. In particular, acidic solutions have less available ions that might hold the analytes within the sample.

The invention may be employed for screening the sample matrix after collection of the sample but prior to sample preparation. In particular, FIG. 1b depicts the vessel 110 oriented such that the sample is in contact with the stationary phase coating 145 located on the bottom portion of the vessel 110 and a detection mechanism 150 employed for illuminating any reactions occurring between the stationary phase coating 145 and the analytes of interest. A negative indication suggests discarding the sample prior to sample preparation and/or detailed analysis in an analytical instrument. Through such "field screening" the probability of analyzing only those samples containing analytes of interest is increased. Additionally, the invention advantageously provides for screening a sample in the same vessel employed for collecting and sample preparation.

FIG. 1c depicts a plurality of vessels 110 containing samples in a container 160 for transportation to a laboratory for sample preparation. Barcode identification labels 170 may be placed on each vessel for identifying the sample and collection history. The vessels are oriented such that during transport, the analytes of interest are provided the opportunity to partition from the sample into the stationary phase such that an equilibrium condition is established.

Figure 2B:
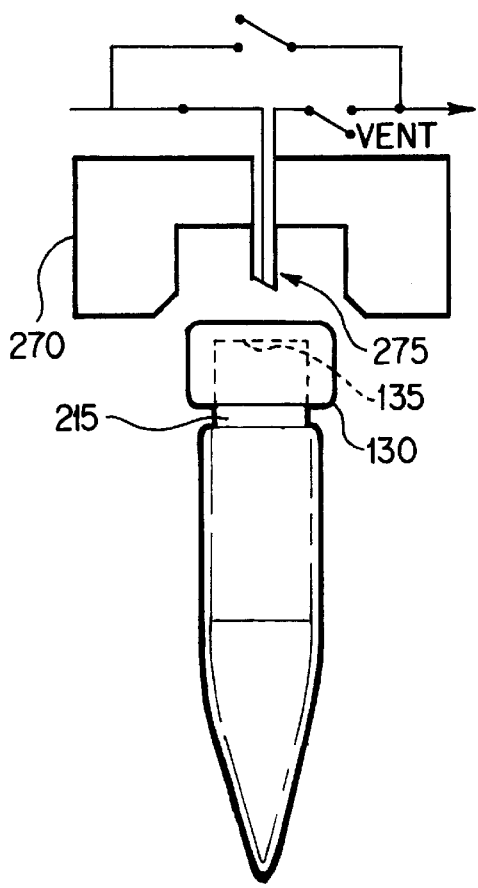
FIG. 2b depicts another simplified schematic of the vessel of FIG. 2a and a heater block.

FIG. 2a depicts a vessel 110 having a cap 130 with a stationary phase coating 140. The vessel is first filled by for example, immersion in a sample 120. A portion of the sample may be poured off such that a headspace 215 is formed above the sample after securing the cap 130 (FIG. 2b). Alternative techniques for filling may be employed, such as a dispensing needle for introducing the sample directly into the vessel. After the sample is introduced into the vessel, the vessel is inverted such that the sample is placed into contact with the stationary phase coating 140 until the analytes of interest from the sample reach an equilibrium condition.

FIG. 2b depicts the vessel 110 positioned with the cap in the upward position such that a headspace 215 is formed above the sample and adjacent to the stationary phase coating on the cap. If the vessel 110 is completely filled with sample and a cap 130 is employed that does not displace a known volume, the dispense needle 275 may be employed for removing a portion of the sample to create a headspace.

Figure 2C:
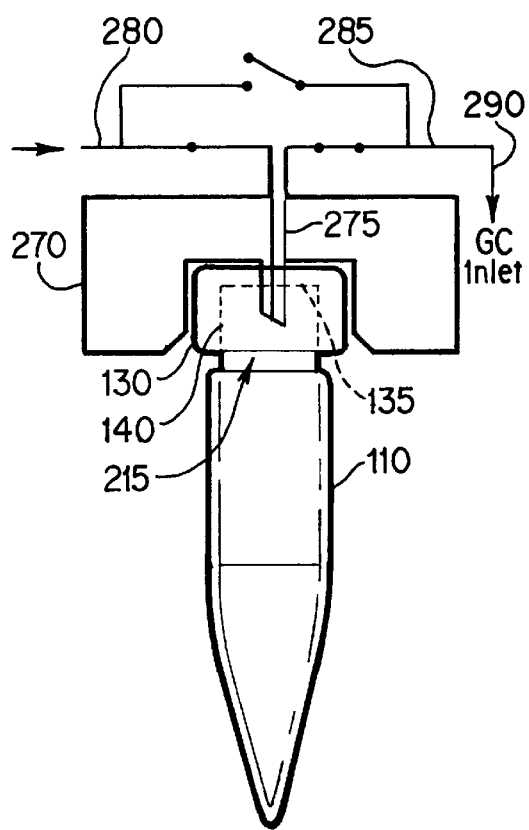
FIG. 2c depicts another simplified schematic of the embodiment of FIG. 2a attached to the heater block.

A venting heater block 270, having a concentric needle 275 for piercing the septum 135 of the cap may be employed for heating the stationary phase to speed up desorption of the analytes of interest into the headspace. Additionally, the heating results in expansion of the headspace and sample causing a pressure increase within the vessel. This pressure may be employed for aspirating the headspace. If the analytes of interest are highly volatile, heating may not be required but can be employed for increasing the rate of adsorption. FIG. 2c depicts the vessel 110 illustrated in FIG. 2a having the heater block 270 mounted on the cap 130. The needle 275 has pierced the septum 135 and is positioned for aspirating the headspace 215. Electrical current is applied to the heater block 270 to heat the stationary phase 140 and desorb the analytes of interest. Once an equilibrium has become established, the headspace is aspirated by carrier gas flow through the inlet portion of the tubing 280 and out of the outlet portion of the tubing 285 for injection into an inlet 290 of an analytical instrument. Alternatively, a non-oxidizing headspace may be formed by introducing a non-oxidizing gas such as nitrogen into the vessel through the needle 275. The aspirated headspace is introduced directly into an analytical instrument for quantitative analysis of the analytes of interest. U.S. Pat. No. 5,363,707 entitled "Headspace Sampling System" discloses a variety of techniques for conducting headspace analysis and is hereby incorporated by reference.

Figure 3A:
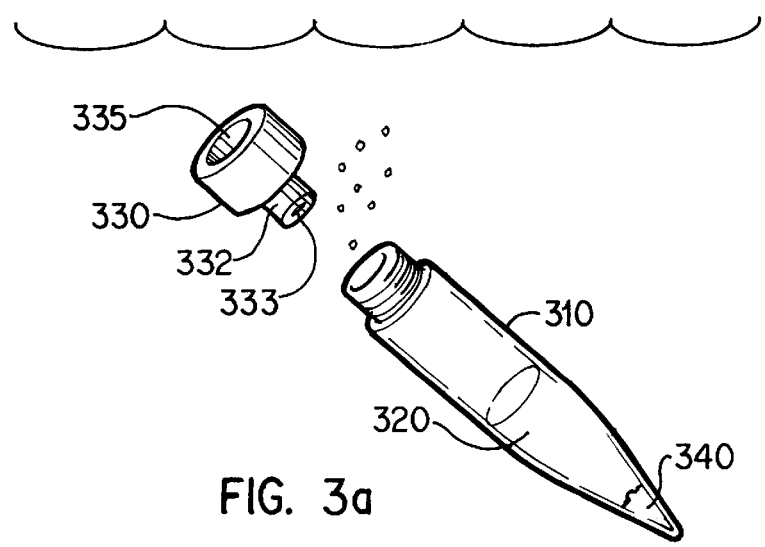
FIG. 3a depicts an alternative embodiment of a vessel having a stationary phase coating on the bottom portion of the vessel.

FIG. 3a depicts an alternative embodiment employing a vessel 310 having a known volume V1. A cap 330 is formed with a cavity 332 that displaces a known volume Vg of sample when inserted into the vessel 310. A membrane 333 provides a temporary seal to insure that the sample is displaced out of the vessel 310 by a known amount corresponding to the volume of the cavity 332 such that a known volume of sample Vc (V1−Vg) remains in the vessel 310. A stationary phase coating 340 is placed on the inside surface of the bottom of the vessel. The concentration of the analyte of interest (Co) in the sample 320 is proportional to the concentration of the analytes of interest within the headspace and the ratio of the headspace volume Vg to the sample volume Vc (Co=Cg [K+(Vg/Vc)] where K is a constant).

Figure 3B:
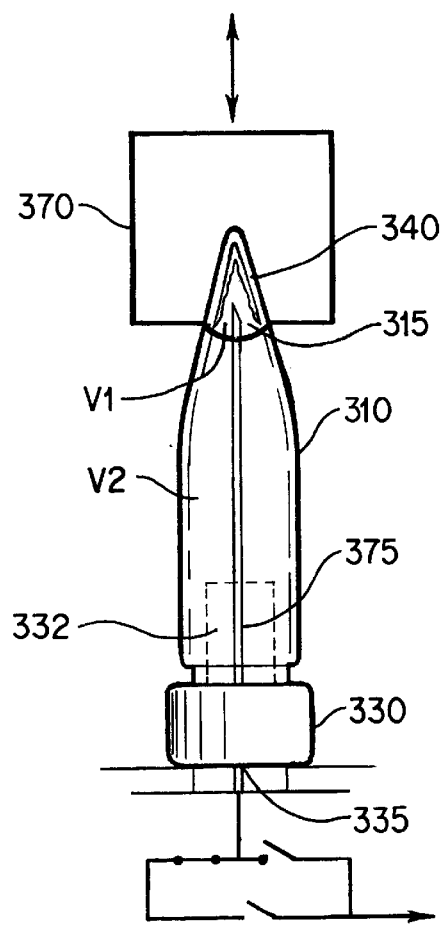
FIG. 3b depicts the vessel in FIG. 3a and a heating block for heating the bottom portion and a venting mechanism that pierces the cap and aspirates the headspace.

FIG. 3b illustrates the vessel 310 in an inverted position and a dispense needle 375 inserted through the septum 335 to break the membrane 333 such that a known volume of sample flows into the cavity 332. A headspace 315, having a headspace volume (V1) corresponding to the amount of sample in the cavity 332, is formed above the sample and in contact with the stationary phase coating 340. A heater block 370 is placed in contact with the vessel 310 and adjacent to the stationary phase coating 340. Electric current is applied to the heater block 370 and the analytes of interest are desorbed from the stationary phase coating 340. Once an equilibrium condition is achieved, the dispense needle 375 is employed for aspirating the headspace for introduction into an analytical instrument.

Figure 4A:
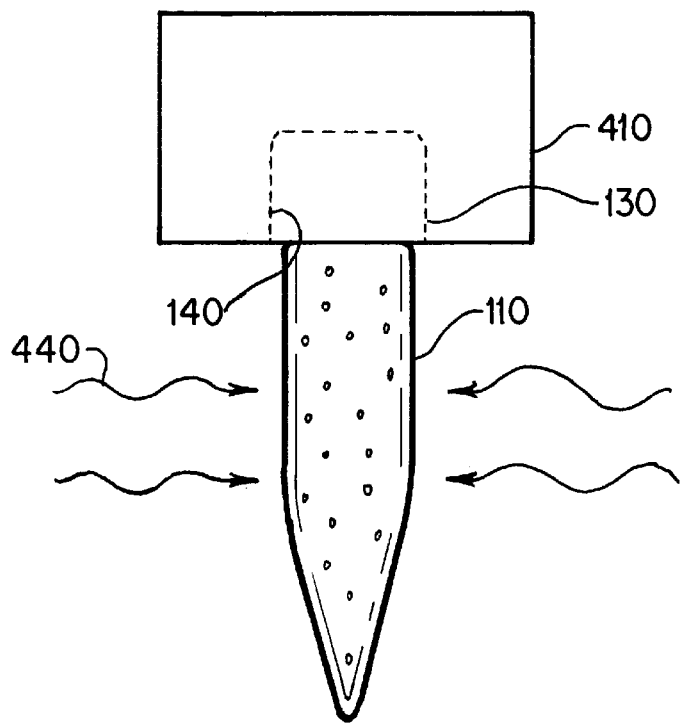
Figure 4B:
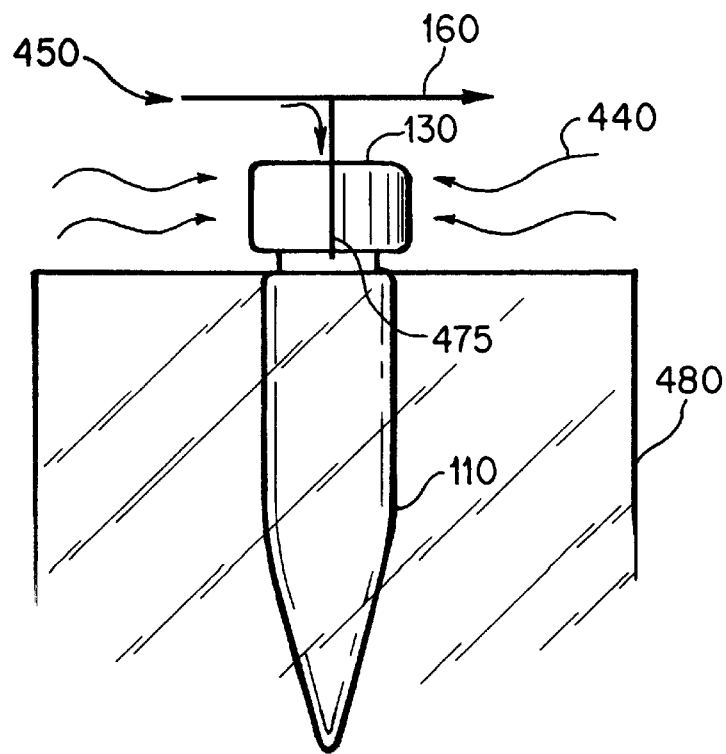
FIG. 4b depicts microwave energy employed for heating the cap of the vessel of FIG. 4b.

In another embodiment depicted in FIG. 4a and FIG. 4b, microwave energy is employed as an alternative means for heating the vessel 110 and cap 130. In FIG. 4a, a microwave shield 410 is placed over the cap 130 while the vessel is exposed to microwave radiation. The microwave energy heats the sample such that analytes of interest are released from suspended solids making up the sample, and are adsorbed into the stationary phase coating 140 on the inside surface of the cap 130. In FIG. 4b, microwave energy is applied to the cap 130 and in particular, the stationary phase coating 140 to desorb the analytes of interest. The desorbed analytes are aspiration by forcing a purge gas 450 through a concentric needle 475 and injected directly into the injection port 160 of a gas chromatograph. As previously discussed, the pressure increase resulting from expansion of the sample upon heating may be employed for aspiration. A microwave shield 480 may also be employed for shielding the vessel 110 from microwaves.

The invention provides for a method and apparatus for collection and preparation of a sample in a sealed vessel having a stationary phase coating that adsorbs analytes of interest such that both sample collection and sample preparation may advantageously be carried out in the sample vessel with out contamination. The vessel includes a cap having a septum for sealing the vessel and for providing access to a headspace formed above the sample. After adsorption, the vessel is oriented such that analytes of interest may be desorbed from the stationary phase coating into the headspace for aspiration by a sampling needle and for introduction into the gas chromatograph. The invention advantageously provides a solventless method for sample screening and sample preparation in one vessel that is not susceptible to contamination.

While the invention has been described with respect to various specific examples and embodiments thereof, it is to be understood that the invention is not limited thereto and that it can be variously practiced within the scope of the following claims. For example, standard 2 ml or larger sample vials may be employed as vessels for holding the sample.

What is claimed is:

1. An apparatus for sample preparation in which a headspace containing analytes of interest adsorbed from a sample stored in a sealed vessel are removed and introduced into a gas chromatograph, comprising:

a vessel into which the sample is stored, the vessel further comprising a cap having a septum for sealing and providing access to the vessel, a stationary phase coating formed on substantially all of the inside surface of the vessel such that in a first orientation, at least a portion of the stationary phase is in contact with the sample such that analytes of interest may be adsorbed into that portion of the stationary phase coating that is in contact with the samples, and wherein, after the analytes of interest are adsorbed, the vessel may be oriented in a second orientation such that a headspace is placed into contact with the stationary phase coating previously in contact with the sample such that analytes of interest are enabled to desorb into the headspace.

2. The apparatus as claimed in claim 1, further comprising a means for heating the vessel to increase the rate of desorption of analytes of interest from the stationary phase into the headspace.

3. The apparatus as claimed in claim 2, the stationary phase being located upon the bottom portion of the vessel.

4. The apparatus as claimed in claim 3, further comprising the steps of:

inverting the vessel after the analytes of interest have reached an equilibrium condition between the sample and the stationary phase coating, wherein a headspace is formed on top of the sample in contact with the stationary phase coating, and inserting a sampling needle through the septum and into the headspace after the analytes of interest have reached equilibrium between the headspace and the stationary phase coating, and aspirating the headspace such that it can be introduced into the gas chromatograph.

5. The apparatus as claimed in claim 4, the cap further comprising a cavity displacing a known volume and a membrane that can be ruptured such that when the vessel is inverted and the membrane is ruptured, sample of a known volume fills the cavity such that the headspace formed on top of the sample is of a known volume.

6. The apparatus as claimed in claim 5, further comprising the step of calculating the concentration of the analytes of interest within the sample as:

$$Co=Cg[k+(Vg/Vc)]$$

where:

Co is the concentration of analytes within the sample,

Cg is the concentration of analytes in the headspace, k is a constant,

Vg is the volume of the headspace, and

Vc is the volume of the sample.

7. The apparatus as claimed in claim 1, the sampling needle further comprising two hollow needles, a first needle for providing a positive gauge pressure into the vessel, and a second needle to aspirate the headspace.

8. The apparatus as claimed in claim 7, wherein the sampling needle further comprises two concentric needles.

9. The apparatus as claimed in claim 7, the positive gauge pressure further comprising the non-oxidizing gas nitrogen.

10. The apparatus as claimed in claim 1, further comprising a detector for illuminating the vessel such that samples containing analytes of interest are identified, wherein samples not containing any analytes of interest may be discarded without further sample preparation.

11. The apparatus as claimed in claim 1, further comprising a stationary phase bonded to the inside surface of the cap, and further comprising the steps of:

introducing a sample into the vessel, securing the cap onto the vessel, inverting the vessel such that the sample is placed in contact with the stationary phase coating such that an equilibrium is formed, inverting the vessel again such that a headspace is placed in contact with the stationary phase coating, and aspirating the headspace after the analytes of interest have desorbed from the stationary phase coating.

12. The apparatus as claimed in claim 11, wherein the cap is secured prior to introducing the sample into the vessel, and wherein, the sample in introduced into the sealed vessel through the septum.

13. A method for sample preparation in which analytes of interest are removed from a sample being stored in a sealed vessel for introduction into a gas chromatograph, comprising:

coating a portion of the inside surface of the vessel with a stationary phase having an affinity for analytes of interest, placing a sample into the vessel and sealing with a cap having a septum, orienting the vessel such that the sample is in contact with the stationary phase coating, waiting until analytes of interest are adsorbed into the stationary phase coating, orienting the vessel such that a headspace is formed in contact with the stationary phase coating such that analytes of interest are desorbed into the headspace, placing a sampling needle through the septum, aspirating the headspace from the vessel, introducing the aspirated headspace into the gas chromatograph.

14. The method as claimed in claim 13, further comprising the step of heating the vessel to increase the rate of desorption of analytes of interest from the stationary phase into the headspace.

15. The method as claimed in claim 14, further comprising microwave energy for heating.

16. The method as claimed in claim 13, further comprising the step of creating a headspace having a known volume in a vessel having a known volume such that concentration of the analytes of interest within the sample can be calculated as:

$$Co=Cg[k+(Vg/Vc)]$$

where:

Co is the concentration of analytes within the sample,

Cg is the concentration of analytes in the headspace, k is a constant,

Vg is the volume of the headspace, and

Vc is the volume of the sample.

17. The method as claimed in claim 13, wherein, the sampling needle further comprises a first and second concentric hollow needle, and further comprises the method steps of:

providing a positive gauge pressure into the vessel through the first concentric needle such that the headspace is aspirated out through the second needle.

18. The method as claimed in claim 13, further comprising the step of screening the sample for the presence of analytes of interest prior to the step of aspirating the headspace.

19. An apparatus for sample preparation in which a headspace containing analytes of interest adsorbed from a sample stored in a sealed vessel are removed and introduced into a gas chromatograph as claimed in claim 1, the stationary phase coating being formed on at least a portion of the inside surface of the vessel.

* * * * *